(12) United States Patent
Gerber et al.

(10) Patent No.: US 7,415,308 B2
(45) Date of Patent: Aug. 19, 2008

(54) IMPLANTABLE MEDICAL DEVICE PROVIDING ADAPTIVE NEUROSTIMULATION THERAPY FOR INCONTINENCE

(75) Inventors: Martin T. Gerber, Maple Grove, MN (US); John C Rondoni, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 215 days.

(21) Appl. No.: 11/117,062

(22) Filed: Apr. 28, 2005

(65) Prior Publication Data

US 2006/0190051 A1 Aug. 24, 2006

Related U.S. Application Data

(60) Provisional application No. 60/655,561, filed on Feb. 23, 2005.

(51) Int. Cl.
A61N 1/00 (2006.01)
(52) U.S. Cl. .......................................... 607/41; 607/40
(58) Field of Classification Search ................. 607/40, 607/41, 133, 138
See application file for complete search history.

(56) References Cited

U.S. PATENT DOCUMENTS

| | | | |
|---|---|---|---|
| 4,106,511 A | 8/1978 | Erlandsson | |
| 4,153,059 A | 5/1979 | Fravel et al. | |
| 4,785,828 A | 11/1988 | Maurer | |
| 4,873,996 A | 10/1989 | Maurer | |
| 5,199,443 A | 4/1993 | Maurer et al. | |
| 5,314,465 A | 5/1994 | Maurer et al. | |
| 5,376,206 A | 12/1994 | Maurer et al. | |
| 5,562,717 A | 10/1996 | Tippey et al. | |
| 5,667,615 A | 9/1997 | Maurer et al. | |
| 5,836,994 A | 11/1998 | Bourgeois | |
| 5,984,854 A | 11/1999 | Ishikawa et al. | |
| 6,026,326 A | 2/2000 | Bardy | |
| 6,061,596 A | 5/2000 | Richmond et al. | |
| 6,091,992 A | 7/2000 | Bourgeois et al. | |
| 6,104,955 A | 8/2000 | Bourgeois | |
| 6,115,635 A | 9/2000 | Bourgeois | |
| 6,238,423 B1 | 5/2001 | Bardy | |
| 6,354,991 B1 | 3/2002 | Gross et al. | |
| 6,366,814 B1 | 4/2002 | Boveja et al. | |
| 6,393,323 B1 | 5/2002 | Sawan et al. | |
| 6,505,074 B2 | 1/2003 | Boveja et al. | |
| 6,652,449 B1 | 11/2003 | Gross et al. | |
| 6,658,297 B2 | 12/2003 | Loeb | |
| 6,659,936 B1 | 12/2003 | Furness et al. | |
| 6,836,684 B1 | 12/2004 | Rijkhoff et al. | |
| 6,853,862 B1 | 2/2005 | Marchal et al. | |
| 6,941,171 B2 * | 9/2005 | Mann et al. | 607/39 |
| 7,203,548 B2 * | 4/2007 | Whitehurst et al. | 607/39 |
| 2005/0060007 A1 | 3/2005 | Goetz | |
| 2005/0060008 A1 | 3/2005 | Goetz | |

(Continued)

Primary Examiner—Carl H. Layno
Assistant Examiner—Brian T Gedeon
(74) Attorney, Agent, or Firm—William D. Bauer

(57) ABSTRACT

In general, the disclosure is directed to an implantable neurostimulator and system capable of providing adaptive neurostimulation therapy to alleviate incontinence. The neurostimulator operates according to a set of stimulation parameters stored in memory. During operation, information is obtained from the patient, the implanted neurostimulator, one or more implanted sensors, or some combination thereof. A processor analyzes the information to automatically generate proposed adjustments to the stimulation parameters applied by the neurostimulator. The adjustments provide an adaptive neurostimulation therapy that supports or enhances therapeutic efficacy based on the information.

22 Claims, 6 Drawing Sheets

U.S. PATENT DOCUMENTS

2005/0060009 A1    3/2005   Goetz
2005/0060010 A1    3/2005   Goetz
2005/0113881 A1 *  5/2005   Gross et al. .................. 607/41

* cited by examiner

IMPLANTABLE MEDICAL DEVICE PROVIDING ADAPTIVE NEUROSTIMULATION THERAPY FOR INCONTINENCE

PRIORITY

This applications claims priority from U.S. Provisional Application No. 60/655,561 filed on Feb. 23, 2005 entitled "IMPLANTALBE MEDICAL DEVICE PROVIDING ADAPTIVE NEUROSTIMULATION THERAPY FOR INCONTINENCE", the disclosure of which is incorporated in its entirety by reference herein.

TECHNICAL FIELD

The invention relates to implantable medical devices and, more particularly, devices for delivering neurostimulation therapy for incontinence.

BACKGROUND

Many people suffer from involuntary urine leakage, i.e., urinary incontinence. Others may suffer from blocked or restricted urine flow. Other urinary disorders include frequent urination, sudden urges to urinate, problems starting a urine stream, painful urination, problems emptying the bladder completely, and recurrent urinary tract infections. A physician uses an urodynamic test to study how a patient stores and releases urine. During the test, the physician obtains urodynamic information based on one or more physiological conditions within the urinary tract.

Different muscles, nerves, organs and conduits within the urinary tract cooperate to collect, store and release urine. A variety of disorders may compromise the urinary tract performance and contribute to incontinence or restricted flow. Many of the disorders may be associated with aging, injury or illness. For example, aging can often result in weakened sphincter muscles, which cause incontinence, or weakened bladder muscles, which prevent complete emptying. Some patients also may suffer from nerve disorders that prevent proper triggering and operation of the bladder or sphincter muscles.

Neurostimulation therapy is applied to alleviate symptoms associated with a variety of pelvic floor disorders including urinary incontinence. An implantable neurostimulator applies electrical stimulation pulses to sacral or pudendal nerves to provide bladder control. The neurostimulator may include a stimulation pulse generator and one or more leads carrying electrodes for delivery of the stimulation pulses to nerve tissue. An external monitor/programmer communicates with the implanted neurostimulator by wireless telemetry to set stimulation parameters such as frequency, pulse width, amplitude and duration, and start and stop stimulation to permit voluntary voiding.

Stimulation parameters are typically loaded into the neurostimulator or external monitor/programmer at a clinic. The parameters may be organized as one or more distinct programs that can be selected using the external monitor/programmer. Also, the external monitor/programmer may permit a patient to adjust one or more individual parameters. The parameters may be reprogrammed in a subsequent clinical visit if the results provided by existing parameters are unsatisfactory.

Existing systems such as these could benefit from more frequent, and/or more logical changes to the stimulation parameters based on individual patients.

SUMMARY

In general, the invention is directed to an implantable neurostimulator and system capable of providing adaptive neurostimulation therapy to alleviate fecal or urinary incontinence. The neurostimulator operates according to a set of stimulation parameters stored in memory. During operation, information is obtained from the patient, the implanted neurostimulator, one or more implanted sensors, or some combination thereof. A processor analyzes the information to automatically generate proposed adjustments to the stimulation parameters applied by the neurostimulator. The processor's analysis is based on generally on adaptive logic. The adjustments provide an adaptive neurostimulation therapy that supports or enhances therapeutic efficacy based on the information obtained.

The information obtained during the method may indicate a level of efficacy achieved by the neurostimulation therapy. For example, the information may include voiding event information that identifies voiding attempts, involuntary leakage episodes, episodes of discomfort (e.g. bladder discomfort), or other incontinence symptoms or characteristics. In addition, the information may include physiological conditions such as pressure, flow, and contractile force. Alternatively, the information may indicate a physiological state of the patient, such as an activity type (e.g., working, driving, sleeping), activity level (e.g., strenuous, moderate, or resting), or posture (standing, sitting, lying down).

The processor applies a set of adaptation logic to the gathered information to formulate proposed adjustments to the stimulation parameters. The processor can automatically program the implanted neurostimulator to apply the adjusted stimulation parameters, or provide the patient with the option of selecting the new stimulation parameters. Alternatively, the processor may present the proposed adjusted stimulation parameters to a healthcare provider for approval prior to programming the neurostimulator. The external monitor/programmer can include the processor that performs the analysis and associated adjustments. In other embodiments, the external monitor/programmer transmits the information to a processor in a remote location, a remote programmer, which analyzes the information and generates the adjustments. Alternatively, the processor can be included in the implantable neurostimulator or sensor(s) if utilized.

In one embodiment, the invention provides a method comprising receiving, in an external programmer, information relating to efficacy of neurostimulation therapy delivered by an implanted neurostimulator to manage urinary or fecal incontinence, adjusting, in a processor one or more stimulation parameters of the neurostimulation therapy based on the received information, and inputting the adjusted parameters from the processor to the implanted neurostimulator.

The details of one or more embodiments of the invention are set forth in the accompanying drawings and the description below. Other features, objects, and advantages of the invention will be apparent from the description and drawings, and from the claims.

DETAILED DESCRIPTION

Embodiments of the invention can be utilized to provide therapy and/or affect pelvic floor disorders. Examples of pelvic floor disorders that can be treated using a device and/or method of the invention include, but are not limited to, urinary control disorders, and fecal control disorders. In one embodiment of the invention, urinary incontinence, fecal incontinence, or some combination thereof are treated using devices and/or methods of the invention.

Embodiments of the invention provide therapy for the various pelvic floor disorders through stimulation of one more nerves of the pelvic floor. Examples of these nerves include, but are not limited to, the sacral nerves, and the pudendal nerves. In one embodiment, the sacral nerves are simulated, in another, the pudendal nerves are stimulated, and in yet another embodiment, both the sacral and pudendal nerves are stimulated.

Figure 1:
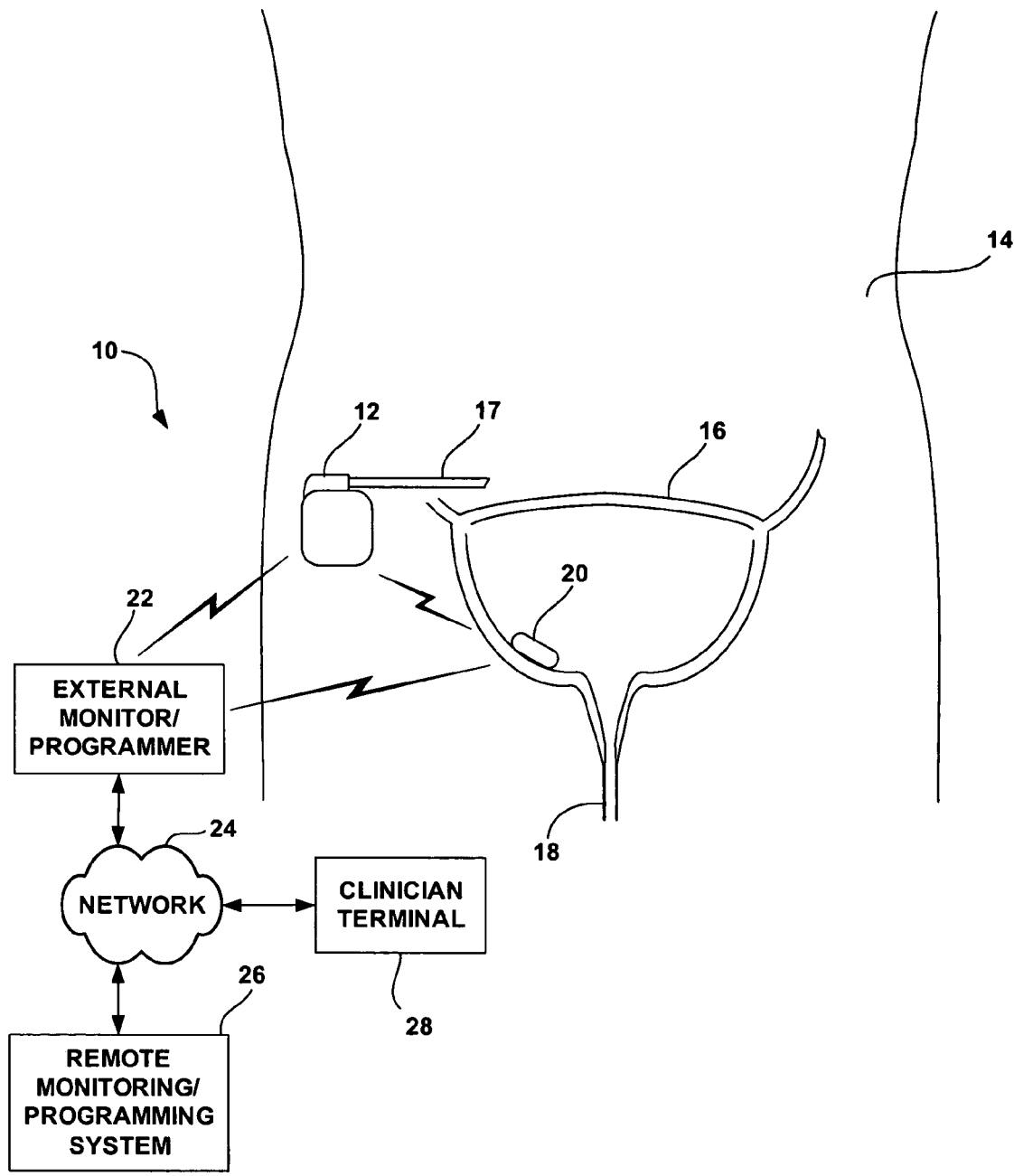
FIG. 1 is a schematic diagram illustrating a neurostimulation system providing adaptive neurostimulation therapy for incontinence.

FIG. 1 is a schematic diagram illustrating a neurostimulation system 10 providing adaptive neurostimulation therapy for incontinence. As shown in FIG. 1, system 10 includes an implantable neurostimulator 12. Neurostimulator 12 is implanted within patient 14 to deliver neurostimulation therapy for control of the function of bladder 16. Neurostimulator 12 may include at least one lead 17 carrying one or more electrodes for delivery of neurostimulation pulses to sacral nerves within the pelvic floor of patient 14. One embodiment includes an implanted urodynamic sensor 20 within bladder 16 to sense physiological conditions such as flow, pressure, contractile force and the like. Sensor 20 may be implanted within bladder 16, urethra 18 or elsewhere within the body of patient 14. Also, in some embodiments, multiple sensors 20 may be implanted within patient 14.

In embodiments that include sensor 20, neurostimulator 12 may receive information from sensor 20 via wireless telemetry. In addition, an external monitor/programmer 22 may receive information from neurostimulator 12 and/or sensor 20 by wireless telemetry. In alternative embodiments, sensor 20 may be integrated within the housing of neurostimulator 12 or coupled to the neurostimulator 12 via one or more leads. External monitor/programmer 22 also may transmit information to neurostimulator 12, such as adjustments to stimulation parameters to be applied by the neurostimulator 12. The adjustments may be made based on the information received from neurostimulator 12, sensor 20, patient 14, or some combination thereof. For example, external monitor/programmer 22 may take the form of a patient programmer that receives information from patient 14 as user input provided via a user interface.

External monitor/programmer 22 may record the received information, analyze the information, and adjust stimulation parameters based on the information or some combination thereof. Alternatively, external monitor/programmer 22 may record information and transmit the information to a remote monitoring/programming system 26 via a network 24. In this case, remote monitoring/programming system 26 analyzes the information to generate adjustments to stimulation parameters, and transmits the adjustments to external monitor/programmer 22 for application to neurostimulator 12. One of skill in the art will also understand and appreciate that a processor responsible for analyzing the received information and proposing or instituting adjusted stimulation parameters could also be associated with the neurostimulator 12. As used herein, associated with refers to a structure that is either housed with or within a device, or attached to a device via a lead. In this case, the information from external monitor/programmer 22 and sensor 20, if applicable, would be transmitted to the processor associated with neurostimulator 12 via wireless telemetry.

One or more clinician terminals 28 may be coupled to network 24 to receive or access notifications of stimulation parameter adjustments generated by external monitor/programmer 22 or remote monitoring/programming system 26. In one embodiment, a clinician terminal 28 can be used by a clinician to reject or approve stimulation parameter adjustments. In the case of approval, external monitor/programmer 22 proceeds to make the adjustments to the stimulation parameters by downloading or inputting the adjustments to implanted neurostimulator 12, e.g., as a new stimulation program, new parameters, or parameter adjustments. Alternatively, the clinician may require a clinical visit by patient 14 so that the clinician may supervise the parameter adjustments using a physician programmer.

Network 24 may take the form of a local area network, wide area network or global network such as the Internet. Remote monitoring/programming system 26 may include a web server to generate web pages containing proposed parameter adjustments for viewing via clinician terminal. In addition, remote monitoring/programming system 26 may include an email server for delivery of email notifications of proposed parameter adjustments. Clinician terminal 28 may be any client device coupled to network 24, such as a personal computer, personal digital assistant, interactive television, mobile telephone, or the like. Using clinician terminal 28, a clinician accesses web pages generated by remote monitoring/programming system 26 and receives email notifications advising the clinician of new information or proposed parameter adjustments for patient 14.

If external monitor/programmer 22 handles analysis of information and generation of proposed parameter adjustments, the adjustments and information still may be transmitted to remote monitoring/programming system 26 so that a clinician may review the information and adjustments via clinician terminal 28. In this case, external monitor/programmer 22 provides the intelligence for analysis and adjustment, but remote monitoring/programming system 26 supports reporting and approval, if necessary, prior to implementation of the adjustments. In other embodiments, remote monitoring/programming system 26 provides the intelligence for analysis and adjustment, as well as the reporting and approval mechanism. In this case, external monitor/programmer 22 serves as a conduit for collection and transmission of patient information and programming of implanted neurostimulator 12 to implement stimulation parameter adjustments. In some embodiments, clinician approval will only be necessary for certain stimulation parameter adjustments for example adjustments of a greater magnitude than a pre-determined limit.

In some embodiments, stimulation parameter adjustments may be made automatically by external monitor/programmer 22, either independently or at the direction of remote monitoring/programming system 26. In many circumstances, however, it will be desirable to obtain clinician approval prior to downloading or inputting stimulation parameter adjustments into neurostimulator 12. For this reason, it is desirable that remote monitoring/programming system 26 supports the generation of notifications and web pages containing detailed reports so that the clinician has the information necessary to make a decision concerning stimulation parameter adjustment. Remote monitoring/programming system 26 may manage information and parameter adjustment decisions for multiple patients 14 as well as multiple clinicians. In each case, external monitor/programmer 22 and remote monitoring/programming system 26 cooperate to provide adaptive adjustment of stimulation parameters applied by neurostimulator 12 for management of incontinence.

The information obtained by external monitor/programmer 22 may be provided by neurostimulator 12, sensor 20, patient 14, or some combination thereof. In the case of neurostimulator 12, the information may include operational information relating to the stimulation therapy delivered by the neurostimulator 12. Examples of operational information include battery status, charging status, lead impedance, parameter sets applied by neurostimulator 12, telemetry status, time since implant of the neurostimulator 12, and information regarding the elapsed time since the stimulation parameters were adjusted. In some embodiments, the parameter sets can include details regarding the frequency, amplitude, and pulse width of stimulation, cycling parameters, identification of the electrodes being used, and other similar parameters. Also, in some embodiments, implanted neurostimulator 12 may serve to receive information from sensor 20 and forward the information to external monitor/programmer 22. Alternatively, in other embodiments, sensor 20 may transmit information directly to external monitor/programmer 22.

Sensor 20, or multiple sensors, may provide a variety of information indicative of the level of efficacy achieved by the neurostimulation therapy delivered by neurostimulator 12. The information may be any information relating to the function of the bladder 16, or any other segment of the patient's urinary tract, in storing releasing and passing urine. For example, sensor 20 may monitor parameters such as bladder pressure, bladder contractile force, urinary sphincter pressure, urine flow rate, urine flow pressure, voiding amount, and the like.

Other examples of sensed information include urine flow velocity, urine or bladder temperature, impedance, urinary pH, or chemical constituency of the urine. Any of such information may reveal the effect of the neurostimulation therapy on the physiological function of bladder 16, urethra 18 or the urinary sphincter. For example, if sensor 20 indicates excessive pressure, excessive contractile force, or involuntary urine flow (i.e., leakage) in response to a set of stimulation parameters, it may be desirable to dynamically adjust the stimulation parameters to reduce the pressure or contractile force, and thereby enhance efficacy.

In still other embodiments, one or more sensors 20 may be implanted within patient 14 to sense a physiological state of the patient. For example, a sensor may be deployed to sense cardiac activity, respiratory activity, electromyographic activity, or the like, as an indication of patient activity level. Such activity level information, in conjunction with other information, may be useful in determining adjustments to stimulation parameters. Other types of sensors 20 also may detect a posture or activity level of the patient. For example, an accelerometer may detect an elevated activity level, e.g., during exercise, while other sensors may detect whether the patient is sitting, standing or lying down. In addition, some of the information obtained by such sensors, such as respiration activity, may be analyzed to determine, e.g., whether the patient is sleeping.

Information obtained from patient 14 includes information entered into external monitor/programmer 22 via a user interface such as a set of buttons, a keypad, a touchscreen, or other input media. Like the information obtained from sensor 20, the information obtained from patient 14 also may indicate a level of efficacy achieved by the neurostimulation therapy. For example, the information may include information regarding voiding, such as for example voiding event information that identifies urine voiding attempts, involuntary leakage episodes, timing of voiding, flow, or other urinary incontinence symptoms and characteristics. Voiding event information, such as the occurrence or frequency of leakage, may be very helpful in evaluating the efficacy of existing stimulation parameters, and devising parameter adjustments to enhance efficacy. In embodiments of the invention for treating fecal incontinence, for example, the information may include fecal voiding attempts, involuntary fecal voiding, timing of fecal voiding, characteristics of the fecal bolus, or other fecal incontinence characteristics and symptoms.

Other information obtained from patient 14 may indicate a physiological state of the patient, such as an activity type (e.g., working, driving, sleeping), activity level (e.g., strenuous, moderate, or resting), or posture (standing, sitting, lying down). Input such as this can be relevant because the efficacy of particular stimulation parameters may vary as the physiological state of the patient changes. For example, a set of stimulation parameters may be more effective when a patient is lying down than when the patient is sitting. When the patient sits down, for example, additional pressure may be exerted on the bladder. In this case, a dynamic increase in stimulation amplitude or frequency may be desirable to prevent involuntary leakage.

Information regarding urine flow may include for example, strength of flow, stability of flow, ease of instituting flow, and amount of flow. As evidenced by this non-exhaustive list, a number of the relevant types of information are subjective and could be rated by the patient using a relative scale. Urine flow could be input by the user after measuring the voided amount. In embodiments of the invention that utilize sensor(s), voiding volume could be determined by the sensor(s), which could obviate the need for the patient to measure and enter the voiding volume.

Information regarding the comfort of the patient 14 may also be obtained. For example, bladder discomfort can be noted, and rated on a relative scale by the user. IN yet another embodiment, the patient can input information regarding the overall subjective feeling of the patient 14 with respect to the neurostimulation therapy. This input could again be based on rating the overall feeling on a relative scale.

Also, in some embodiments, a patient 14 may be permitted to enter patient preferences, e.g., based on subjective sensations experience by the patient. For example, a patient 14 may enter information indicating that a stimulation level, e.g., amplitude, pulse width or pulse rate, is unpleasant or even painful. In addition, the patient 14 may enter information for stimulation levels that seems to have no perceived efficacy from the patient's perspective. In some embodiments, a patient 14 may also be permitted to enter an overall subjective indication of how they are feeling, or how they perceive the stimulation to be affecting their urological concern, i.e. an indication of overall quality of life with regard to the stimulation therapy.

All of the information obtained by external monitor/programmer 22 or neurostimulator 12 may be temporally correlated so that it is possible to evaluate the conditions experienced by a patient, e.g., at the time of a significant voiding event. For example, if the patient experiences leakage, it may be useful to evaluate the stimulation parameters that were applied at the time of leakage, the activity level of the patient at the time of leakage, the physiological conditions sensed by sensor 20 at the time of leakage, and any recently input subjective indications by patient 14. In this manner, it is possible to ascertain whether a stimulation parameter adjustment should be a global adjustment, or possibly a specific adjustment to a program applied at the time of leakage, such as a stimulation program formulated for periods of rest or exercise.

In response to the information obtained from patient 14, sensor 20, neurostimulator 12, or some combination thereof, the processor applies a set of adaptation logic to the gathered information to formulate proposed adjustments to the stimulation parameters to be applied by neurostimulator 12. As already indicated, the processor functions may be associated with the external monitor/programmer 22, remote monitoring/programming system 26, the neurostimulator 12, the sensor 20, or some combination thereof. The adaptation logic may take the form of a function or set of functions, expressed mathematically or in a lookup table, that weight various informational items with predetermined coefficients and sum the weighted items to produce a parameter adjustment. In one embodiment, the adaptation logic could be based at least in part on some combination of physician- and/or manufacturer-determined safety ranges, efficacy of the stimulation, and battery life. In another embodiment, the adaptation logic includes weighting of all of the information received by the external monitor/programmer 22, the implantable neurostimulator 12, and the sensor 20 if applicable. In a further embodiment, the adaptation logic could also include weighting of other parameters input via a clinician, either through initial programming of the processor, or via a remote monitoring/programming system 26. In one embodiment, the safety ranges, whether clinician-determined, or manufacturer-determined, set the absolute limits of the parameter adjustment and/or are weighted most heavily by the adaptation logic.

The stimulation parameter adjustments may be expressed as an upward or downward change in one or more parameters such as amplitude, pulse width or frequency. The stimulation parameter adjustments may be expressed as an absolute magnitude of adjustment, or an incremental adjustment. In other words, the stimulation parameter adjustments may be applied in a single step in the amount specified by the output of the processor. If the adaptation logic, upon analysis of the information, specifies an increase of 20 Hz in the frequency of the stimulation pulses applied by neurostimulator 12, that 20 Hz increase is proposed as an instant adjustment to the stimulation parameters. In some cases, an absolute adjustment may be limited either by the manufacturer or by a clinician to a maximum adjustment to avoid instantaneous changes that cause abrupt discomfort for patient 14.

Alternatively, the adaptation logic may simply indicate that an increase is necessary, in which case a series of incremental increases are applied at periodic intervals until the adaptation logic no longer indicates the need for an increase. For example, frequency may be increased in 5 Hz increments for so long as the adaptation logic indicates the need for an increase. In this case, a hysteresis function may be built into the logic to avoid repeated up/down toggling of the stimulation parameters. The adjustments may be carried out at different intervals, such as seconds, minutes, hours, and even days, subject to the discretion of a clinician. In addition to increases or decreases in parameters, the adaptation logic also may indicate that the efficacy is within an acceptable range, and provide an output indicating no need for adjustment.

In one embodiment, the processor may also determine and modify, if necessary the frequency of analyzing and adjusting the stimulation parameters. For example, upon implantation, and soon thereafter, more adjustment may be necessary or desirable to obtain the most beneficial stimulation settings. In one embodiment, the timing of when to analyze the stimulation parameters can be determined at least in part by analyzing the history of the stimulation parameters, and adjustment thereof. Alternatively, the timing of the adjustment analysis can be pre-determined by a clinician, the manufacturer, the patient, or some combination thereof. In yet another embodiment, the patient can indicate, based on a subjective analysis of the efficacy of the current parameters, that the processor should analyze the stimulation parameters to determine if an adjustment is necessary.

In embodiments in which external monitor/programmer 22 or remote monitoring/programming system 26 are permitted to directly and automatically adjust the stimulation parameters of neurostimulator 12, the information may be analyzed on a periodic basis, e.g., at intervals on the order of seconds, minutes, hours or days. In some embodiments, external monitor/programmer 22 and remote monitoring/programming system 26 may apply different analysis modes. In a first mode, the information may be analyzed and adjustments made at relatively infrequent periodic intervals on the order of several hours or several days.

In a second mode, external monitor/programmer 22 or remote monitoring/programming system 26 may operate in a more intensive analysis and adjustment mode in which information is evaluated and parameters are adjusted very frequently until a desired level of efficacy is achieved. This second, more intensive mode may continue until the efficacy level is driven into an acceptable range. The intensive mode may be entered when analysis in the first, infrequent mode reveals efficacy levels that require stimulation parameter adjustments. Again, the adjustments made to the stimulation parameters in either mode may be performed automatically or subject to approval by a clinician, patient, or both.

In one embodiment, the processor can, without further input, or authorization from any other source, input and utilize the new stimulation parameters. As discussed above, another embodiment requires approval by a clinician, through a remote monitoring/programming system 26 before the new simulation parameters can be instituted and utilized by the neurostimulator 12. In yet another embodiment, the processor can send the new stimulation parameters to the external monitor/programmer 22 for review and/or approval by the patient 14. In an alternative embodiment, the external monitor/programmer 22 can display the proposed new stimulation parameters, seek patient approval to institute the new stimulation parameters, and maintain the previous stimulation parameters in memory. This embodiment could allow the patient to subjectively compare the efficacy of the two stimulation parameters and pick which settings they prefer. Furthermore, a number of previous stimulation parameters could be stored in memory to allow the patient to pick from them, or designate some as particularly efficacious, particularly undesirable, or particularly efficacious for one or more activity levels or types (i.e. a particularly desirable setting for exercise).

Sensor 20 may be chronically implanted within patient 14 for use over an extended period of time. In this case, sensor 20 carries sufficient battery resources, a rechargeable battery, or an inductive power interface that permits extended operation. Sensor 20 may be implanted by minimally invasive, endoscopic techniques for an extended period of time or a limited period of time to capture information useful in analyzing and adjusting the stimulation parameters. In other words, sensor 20 may be chronically implanted to support ongoing parameter adjustments over an extended course of therapy spanning several months or years, or purposefully implanted for a short period of time to support a one-time parameter adjustment or a small number of adjustments over a relatively short period of time, such as several hours, days or weeks.

In some embodiments, sensor 20 transmits sensed information continuously or periodically to neurostimulator 12 or external monitor/programmer 22. In this case, sensor 20 monitors physiological conditions continuously or periodically. Alternatively, neurostimulator 12 or external monitor/programmer 22 may trigger activation of sensor 20 to capture information at desired intervals. In some cases, triggered activation may occur when patient 14 enters information into external monitor/programmer 22 to indicate a voiding event. Triggered activation of sensor 20 may be useful in conserving battery life, if applicable, of the sensor 20 or neurostimulator 12. In each case, multiple sensors 20 may be provided and dedicated to different parameters or different locations within the urinary tract.

Rather than immediately transmitting the urodynamic information to neurostimulator 12 or external monitor/programmer 22, sensor 20 may initially store the information internally for subsequent wireless transmission. Hence, in some embodiments, the information may be stored within sensor 20, and later transmitted to neurostimulator 12 or external monitor/programmer 22. In this case, neurostimulator 12 or external monitor/programmer 22 may interrogate sensor 20 to obtain the stored information for analysis and possible adjustment of stimulation parameters.

Figure 2:
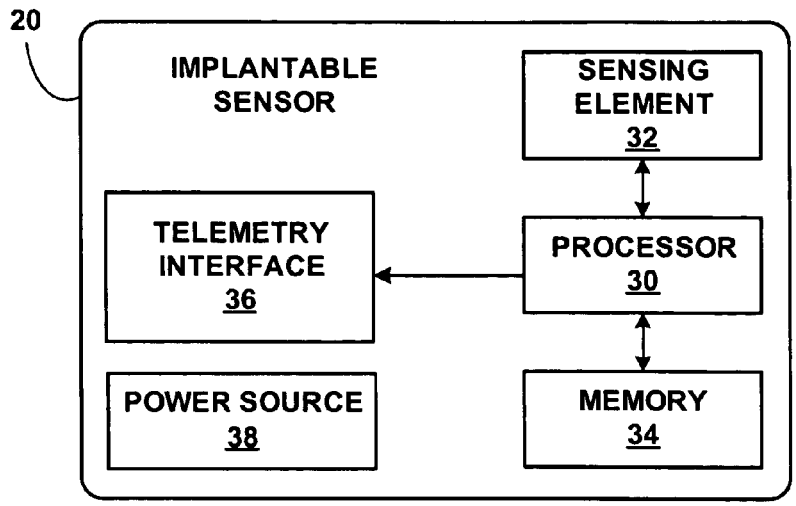
FIG. 2 is a block diagram illustrating an implantable sensor.

FIG. 2 is a functional block diagram illustrating implantable sensor 20 of FIG. 1. In the example of FIG. 2, sensor 20 includes a sensor processor 30, a sensing element 32, memory 34, wireless telemetry interface 36, and a power source 38. Sensor 20 also may include an internal clock to track date and time of voiding events. Sensor 20 may have a capsule-like shape, and may be placed within bladder 14 or urethra 18 by endoscopic introduction via the urethra, or by hypodermic injection using a hypodermic needle. Alternatively, sensor 20 may be surgically implanted. In the case of minimally invasive endoscopic introduction, sensor 20 may be constructed in a manner similar to the sensors described in U.S. patent application Ser. No. 10/978,233, to Martin Gerber, filed Oct. 29, 2004, and entitled "Wireless Urinary Voiding Diary System," which claims the benefit of U.S. provisional application No. 60/589,442, filed Jul. 20, 2004; or U.S. patent application Ser. No. 10/833,776, to Mark Christopherson and Warren Starkebaum, filed Apr. 28, 2004, entitled "Implantable Urinary Tract Monitor," the entire content of each of which is incorporated herein by reference.

Power source 38 may take the form of a small battery. An external source of inductively coupled power may be used, in some embodiments, to power some features of monitor 20, or to recharge the battery. For example, sensor 20 may include an inductive power interface for transcutaneous inductive power transfer to power higher energy functions such as telemetry. However, sensor 20 typically will include a small battery cell within the sensor housing. Alternatively, sensor 20 may include an inductive power interface in lieu of a battery.

Telemetry interface 36 permits wireless communication with external monitor/programmer 22, remote monitoring/programming system 26, or neurostimulator 12 for wireless transmission of information obtained by sensor 20, as well as wireless reception of activation triggers that direct sensor 20 to collect physiological information or transmit stored information. As a further alternative, triggered activation may be applied by patient 14 in the form of a magnet swiped in proximity to sensor 20, in which case the monitor will include appropriate sensing circuitry to detect the magnet.

Sensor processor 30 controls telemetry interface 36 and handles processing and storage of information obtained by sensing element 32. Sensor processor 30 controls operation of sensor 20 and may include one or more microprocessors, digital signal processors (DSPs), application-specific integrated circuits (ASICs), field-programmable gate arrays (FPGAs), or other equivalent logic circuitry. Memory 34 may include any magnetic, electronic, or optical media, such as random access memory (RAM), read-only memory (ROM), electronically-erasable programmable ROM (EEPROM), flash memory, or the like, or a combination thereof. Memory 34 may store program instructions that, when executed by sensor processor 30, cause the controller to perform the functions ascribed to it herein. For example, memory 34 may store instructions for sensor processor 30 to execute in support of control of wireless telemetry interface 36 and control of, and processing of information obtained by, sensing element 32. Memory 34 may include separate memories for storage of instructions and urodynamic information.

Telemetry interface 36 may include a wireless radio frequency (RF) transmitter and receiver to permit bi-directional communication between sensor 20, neurostimulator 12, external monitor/programmer 22, remote monitoring/programming system 26, or some combination thereof. In this manner, external monitor/programmer 22 may transmit commands to sensor 20 for collection of information or collection of information stored in memory 34, and receive status and operational information from the sensor 20. Telemetry interface 36 includes an antenna, which may take a variety of forms. For example, the antenna may be formed by a conductive coil or wire embedded in a housing associated with sensor 20. Alternatively, the antenna may be mounted on a circuit board carrying other components of sensor 20, or take the form of a circuit trace on the circuit board.

Battery power source 38 may take the form of a battery and power generation circuitry. In some embodiments, sensor 20 may be used for a few days or weeks, and therefore may not require substantial battery resources. Accordingly, the battery within battery power source 38 may be very small in some cases. An example of a suitable battery is the Energizer 337 silver oxide cell, available from the Eveready Battery Company, of St. Louis, Mo., USA. The Energizer 337 battery is disc-shaped, and has a diameter of 4.88 mm and thickness of 1.65 mm. Another example battery is the QL0031 3 milliamp cylindrical battery from Quallion, LLC, of Sylmar, Calif., USA, which has a diameter of approximately 2.9 mm and a length of approximately 13.0 mm.

In further embodiments, battery power source 38 may be rechargeable via electromagnetic induction or ultrasonic energy transmission, and includes an appropriate circuit for recovering transcutaneously received energy. For example, battery power source 38 may include a secondary coil and a rectifier circuit for inductive energy transfer. In still other embodiments, battery power source 38 may not include any storage element, and sensor 20 may be fully powered via transcutaneous inductive energy transfer, which may be provided by external receiver 14. In either case, sensor 20 may be constructed for short-term or long-term operation.

Sensing element 32 may be selected for any of a variety of urodynamic testing applications, and may include appropriate signal processing circuitry such as amplifier, filter, driver, and analog-to-digital conversion circuitry for presentation of sensed information to sensor processor 30. For urodynamic testing, sensing element 32 may take the form of a pressure, flow, velocity, volume, temperature, impedance, or contractile force sensor. For pressure measurements, for example, sensing element 32 may include one or more diaphragm sensors, strain gauge sensors, capacitive sensors, piezoelectric sensors, or other sensors used in conventional catheter-based urodynamic testing to sense pressure. As a further example, for bladder emptying, sensing element 32 may include a conductive sensor to sense the presence of urine within the lower region of the bladder 16.

For flow measurements, sensing element 32 may comprise a pulsed Doppler ultrasonic sensor, or a laser Doppler flow sensor. Doppler shifting of the frequency of the reflected energy indicates the velocity of the fluid flow passing over a surface of sensing element 32. Consequently, in some embodiments, sensor 20 may include circuitry, such as a quadrature phase detector, in order to enable the monitor to distinguish the direction of the flow of fluid in addition to its velocity.

As a further example, sensing element 32 may include any one or more thermal-convection velocity sensors. A thermal-convection velocity sensor may include a heating element upstream of a thermistor to heat urine within the urethra 18 such that flow rate may be measured according to the temperature of the heated fluid when it arrives at the thermistor. In other embodiments, flow rate may be determined from the output of a concentration or temperature sensor using Fick's techniques.

In some embodiments, sensing element 32 may include multiple sensors of a given type, as well as multiple types of sensors, e.g., pressure, flow, bladder emptying, or the like. Accordingly, the information obtained by sensor 20 may then include different types of physiological parameters associated with a voiding event. Alternatively, multiple sensors 20 may be deployed within bladder 16 or urethra 18. In this case, each sensor 20 may be configured with a different type or set of sensing elements 32 to collect a variety of different urodynamic parameters during a voiding event.

In some other embodiments, sensing element 32 may be chosen to sense a physiological state, such as an activity type, activity level, or posture of the patient 14. For example, sensing element 32 can include an accelerometer to detect an elevated activity level, or a decreased activity level.

Figure 3:
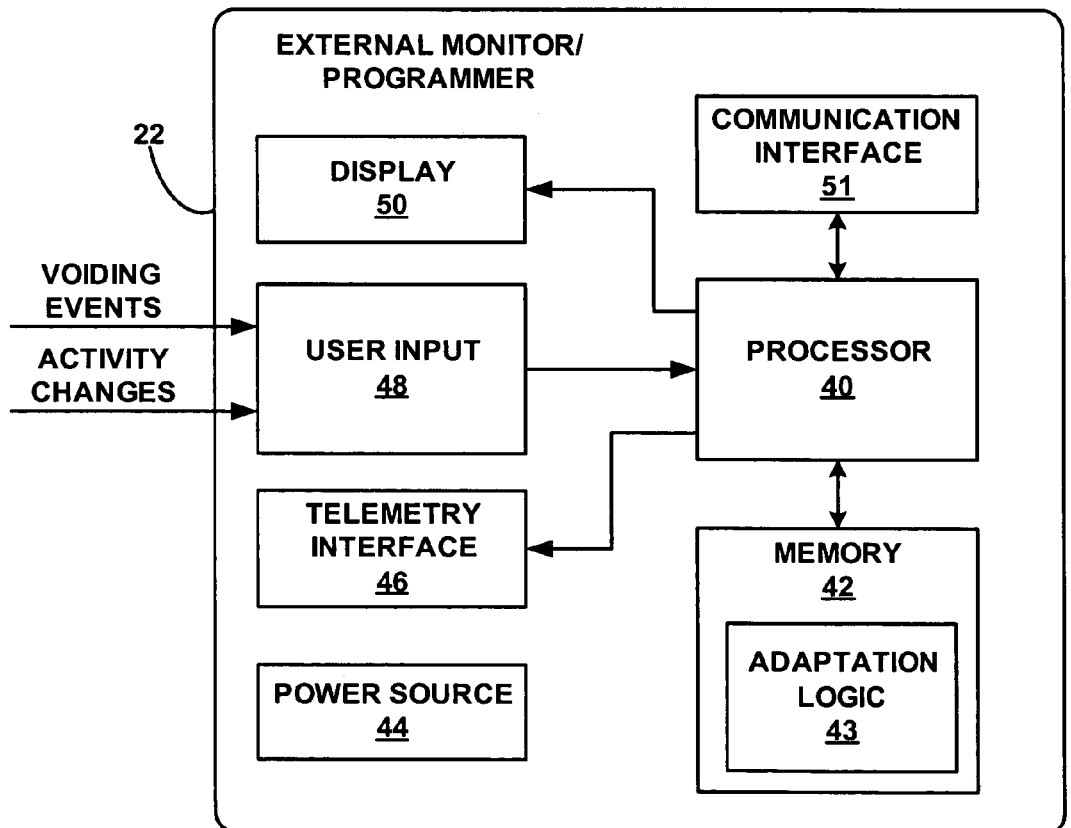
FIG. 3 is a block diagram illustrating an external monitor/programmer.

FIG. 3 is a functional block diagram illustrating external monitor/programmer 22. In the example of FIG. 3, external monitor/programmer 22 includes a processor 40, memory 42, power source 44, telemetry interface 46, user input device 48 and display 50. User input device 48 may take the form of a set of buttons, a keypad, a touchscreen, soft keys on a display, or other input media. Display 50 may be a liquid crystal display (LCD), plasma display, or the like, which conveys status and operational information to the patient 14, and aids the patient in entry of information into external monitor/programmer 22.

Memory 42 stores instructions for execution by processor 40, as well as a set of adaptation logic 43, which may be expressed, e.g., in terms of one or more functions or lookup table entries. In addition, memory 42 may store information received from sensor 20, neurostimulator 12, and patient 14. Memory 36 may include separate memories for storage of instructions and information received from sensor 20, neurostimulator 12 or patient 14. Processor 40 may be constructed in a variety of ways, as described above with respect to sensor processor 30 of FIG. 2, including as one or more microprocessors, an ASIC, an FPGA, or a combination thereof. It should also be understood and appreciated by one of skill in the art that the functions of the processor 40 as described above with respect to the adaptation logic could be undertaken by a similar processor associated with the neurostimulator 12, the sensor 20, the remote monitoring/programming system 26, or some combination thereof. For example, in one embodiment, the information gathered from sensor 20 could be weighted accordingly via adaptation logic stored in memory and carried out by a processor within sensor 20 and then transmitted via wireless telemetry to a processor in external monitor/programmer 22 to incorporate those weighted factors in to the analysis of the stimulation settings.

Processor 40 controls telemetry interface 46 to obtain urodynamic information from sensor 20, neurostimulator 12, or some combination thereof. Processor 40 also may control telemetry interface 46 to receive information from sensor 20 or neurostimulator 12 on a substantially continuous basis, at periodic intervals, or only upon receipt of an activation command. Hence, external monitor/programmer 22 may obtain an ongoing indication of the physiological conditions sensed by sensor 20, or receive periodic updates upon triggered activation of sensor 20. For example, external monitor/programmer 22 may be configured to respond to a voiding event activation command entered by patient 14 via user input device 48. In response to the voiding event activation command, external monitor/programmer 22 generates an activation control signal and transmits the control signal to sensor 20 via telemetry interface 46.

Wireless telemetry may be accomplished by radio frequency (RF) communication or proximal inductive interaction of external monitor/programmer 22 with sensor 20 or neurostimulator 12. Alternatively, telemetry interfaces 36, 46 may be configured for sensor 20 and external monitor/programmer 22 to support radio frequency (RF) communication with a sufficiently strong signal such that proximate interaction is not required. In addition to an RF or inductive telemetry interface 46, external monitor/programmer 22 may include a wired or wireless interface 51 for communication with other external devices, e.g., either directly or via network 24.

External monitor/programmer 22 may take the form of a portable, handheld device, like a pager, cell phone, or patient programmer that can be carried by patient 14. External monitor/programmer 22 may include an internal antenna, an external antenna protruding from the device housing, or an external antenna that extends from the device housing on a cable and is attached to the body of patient 14 at a location proximate to the location of neurostimulator 12 or sensor 20 to improve wireless communication reliability. Also, in some embodiments, external monitor/programmer 22 also may receive operational or status information from neurostimulator 12 or sensor 20, and may be configured to actively configure and interrogate the neurostimulator 12 or sensor 20 to receive the information.

With adaptation logic 43, processor 40 of external monitor/programmer 22 may be programmed to analyze information obtained from neurostimulator 12, sensor 20, or patient 14, and generate proposed adjustments to the stimulation parameters based on the information. Hence, in some embodiments, at least some portion of the intelligence for formulating parameter adjustments may reside within external monitor/ programmer 22. In other embodiments, however, at least a portion of the intelligence may reside within remote monitoring/programming system 26. In other embodiments, at least a portion of the intelligence for formulating stimulation parameter adjustments may reside within neurostimulator 12. In further embodiments, at least a portion of the intelligence for formulating parameter adjustments may reside within the sensor(s) 20. Alternatively, external monitor/programmer 22, remote monitoring/programming system 26, neurostimulator 12, and sensor(s) 20 may provide shared intelligence for analysis of received information and generation of proposed stimulation parameter adjustments.

In some embodiments, external monitor/programmer 22 may generate a voiding diary, substantially as described in the aforementioned U.S. patent application Ser. No. 10/978,233, to Martin Gerber, filed Oct. 29, 2004, and entitled "Wireless Urinary Voiding Diary System." In this case, external monitor/programmer 22 tracks voiding events and other information. As a further variation, in some embodiments, the adaptation logic may be provided within neurostimulator 12. In particular, external monitor/programmer 22 may download to neurostimulator 12, periodically or on demand, information obtained from neurostimulator 12, sensor 20, or the patient through the external monitor/programmer 22, including voiding diary information in some instances. Neurostimulator 12 then may be configured to analyze the information and make stimulation parameter adjustments based on the information, much like external monitor/programmer 22 or remote monitoring/programming system 26. Hence, in this case, analysis and adjustments are made within neurostimulator 12 based on information recorded in external monitor/programmer 22. In still other embodiments, neurostimulator 12 may be configured to implement both recording of information and analysis and stimulation parameter adjustments.

Figure 4:
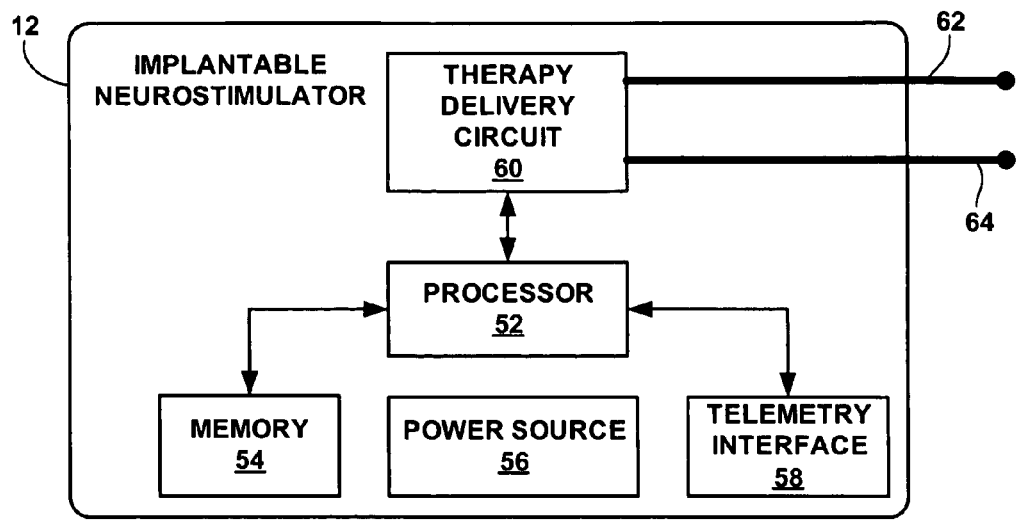
FIG. 4 is a block diagram illustrating an implantable neurostimulator.

FIG. 4 is a block diagram illustrating neurostimulator 12. As shown in FIG. 4, neurostimulator 12 includes a processor 52, memory 54, power source 56, telemetry interface 58, and therapy delivery circuit 60. Memory 54 stores one or more neurostimulation programs that specify neurostimulation parameters for stimulation pulses delivered by therapy delivery circuit 60. The parameters may be adjusted automatically or upon clinician approval by external monitor/programmer 22, which downloads or inputs new programs, new parameters or stimulation parameter adjustments to neurostimulator 12.

In general, the stimulation parameters are selected to have values effective in controlling or managing symptoms of urinary incontinence, such as involuntary leakage. An exemplary range of neurostimulation stimulation pulse parameters likely to be effective in treating incontinence, e.g., when applied to the sacral or pudendal nerves, are as follows:

1. Frequency: between approximately 0.5 Hz and 500 Hz, in another embodiment between approximately 10 Hz and 250 Hz, and in yet another embodiment between approximately 10 Hz and 25 Hz.

2. Amplitude: between approximately 0.1 volts and 50 volts, in another embodiment between approximately 0.5 volts and 20 volts, and in yet another embodiment between approximately 1 volt and 10 volts.

3. Pulse Width: between about 10 microseconds and 5000 microseconds, in another embodiment between approximately 100 microseconds and 1000 microseconds, and in yet another embodiment between approximately 180 microseconds and 450 microseconds.

Therapy delivery circuit 60 drives one or more leads. In the example of FIG. 4, therapy delivery circuit 60 drives electrodes carried by a pair of leads 62, 64. Leads 62, 64 extend from the housing of neurostimulator 12, and have a distal end that extends to target nerve sites within the pelvic floor, such as sacral or pudendal nerve sites. Each lead 62, 64 may carry one or more electrodes, and may be configured as an axial lead with ring electrodes or a paddle lead with electrode pads arranged in a two-dimensional array. The electrodes may operate in a bipolar or multi-polar configuration with other electrodes, or may operate in a unipolar configuration referenced to an electrode carried by the device housing or "can" of neurostimulator 12.

Power source 56 may be a battery, either rechargeable or non-rechargeable. In the case of a rechargeable battery, power source 56 may include an inductive power interface for recharging. In other embodiments, power source 56 may be powered entirely by inductive power transfer from an external power source. Telemetry interface 58 may be constructed and function in a manner similar to telemetry interface 36 of implantable sensor 20 of FIG. 2. Processor 52 may be constructed in a variety of ways, as described above with respect to sensor processor 30 of FIG. 2, including as one or more microprocessors, an ASIC, an FPGA, or a combination thereof.

Figure 5:
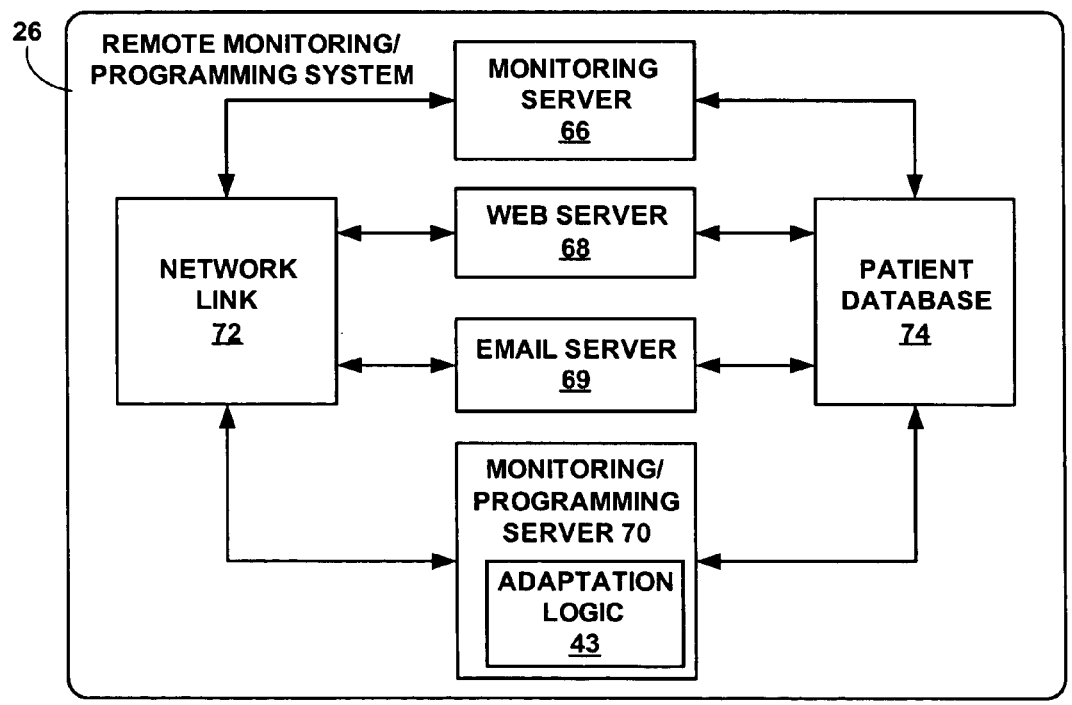
FIG. 5 is a block diagram of a remote monitor/programmer system.

FIG. 5 is a block diagram illustrating a remote monitoring/programming system 26. As shown in FIG. 5, remote monitoring/programming system 26 may include a monitoring server 66, a web server 68, an email server 69, a programming server 70, a network link 72, a patient database 74, or some combination thereof. Monitoring server 66 listens for network traffic over network link 72 from one or more external monitor/programmers 22 associated with various patients, receives information from the external monitor/programmers 22, and records the information in a record in patient database 74. Patient database 74 may store information for multiple patients in an organized form that permits ready retrieval of information for analysis, reporting, and historical archival.

Web server 68 generates web pages that contain information obtained for one or more patients, including information obtained from external monitor/programmers 22. The information may be presented in a variety of formats and levels of detail. Using clinician terminal 28, equipped with a web browser, a clinician can view information contained in patient database 74 by accessing web server 68. Web server 68 also may be configured to execute database access commands to retrieve desired information. In some embodiments, the information may be organized using a hierarchy of XML tags.

The information contained in the web pages also may include proposed stimulation parameter adjustments. The stimulation parameter adjustments may be generated by an external monitor/programmer 22 or remote monitoring/programming system 26. A clinician may approve the stimulation parameter adjustments by clicking on a button within the web page. Upon receipt of clinician approval, remote monitoring/programming system 26 may then proceed to interact with an appropriate external monitor/programmer 22 to implement the stimulation parameter changes in the pertinent neurostimulator 12. The web page generated by web server 68 also may offer the clinician the opportunity to modify the proposed stimulation parameter adjustments before approval, e.g., using boxes, drop down menus, slider bars, radio buttons, or the like. In this case, remote monitoring/programming system 26 implements the stimulation parameter adjustments as modified by the clinician.

Email server 69 provides email notifications to a clinician terminal 28, if desired. The email notifications may report newly acquired information for a particular patient 14, or proposed stimulation parameter adjustments for the patient. The email notifications may include links to web pages for approval or modification of the proposed stimulation parameter adjustments. Alternatively, in some embodiments, the clinician may approve stimulation parameter adjustments by replying to the email notification. In either case, the proposed stimulation parameter adjustments are not implemented until approval is received. In other embodiments, however, it is conceivable that stimulation parameter adjustments may be fully automatic, and not require clinician approval, particularly if stimulation parameter adjustments are subject to preprogrammed limits within the external monitor/programmer or the neurostimulator 12.

Programming server 70 analyzes information obtained from neurostimulator 12, sensor 20, patient 14, or some combination thereof, via external monitor/programmer 22. In particular, like processor 40 of FIG. 3, programming server 70 may apply adaptation logic 43 to determine whether stimulation parameters applied by neurostimulator 12 should be adjusted. If so, programming server 70 generates a set of stimulation parameter adjustments and transmits the adjustments to external monitor/programmer 22, either automatically or upon clinician approval, for download or input to neurostimulator 12.

When a new set of stimulation parameter adjustments is formulated, programming server 70 stores the adjustments in patient database 74. The next time web server 68 accesses database 74 to assemble a web page for viewing by a clinician, the web page will include the stimulation parameter adjustments. For email notifications, programming server 70 or database 74 may generate a command that directs email server 69 to prepare a notification of the new stimulation parameter adjustments for email delivery to clinician terminal 28. Upon approval of the adjustments by the clinician, programming server 70 releases the adjustments to external monitor/programmer 22 for downloading or input to neurostimulator 12. Although programming server 70 formulates the adjustments in the example of FIG. 5, in other embodiments, the programming server may be responsible for presenting adjustments formulated by external monitor/programmer 22 for approval.

Figure 6:
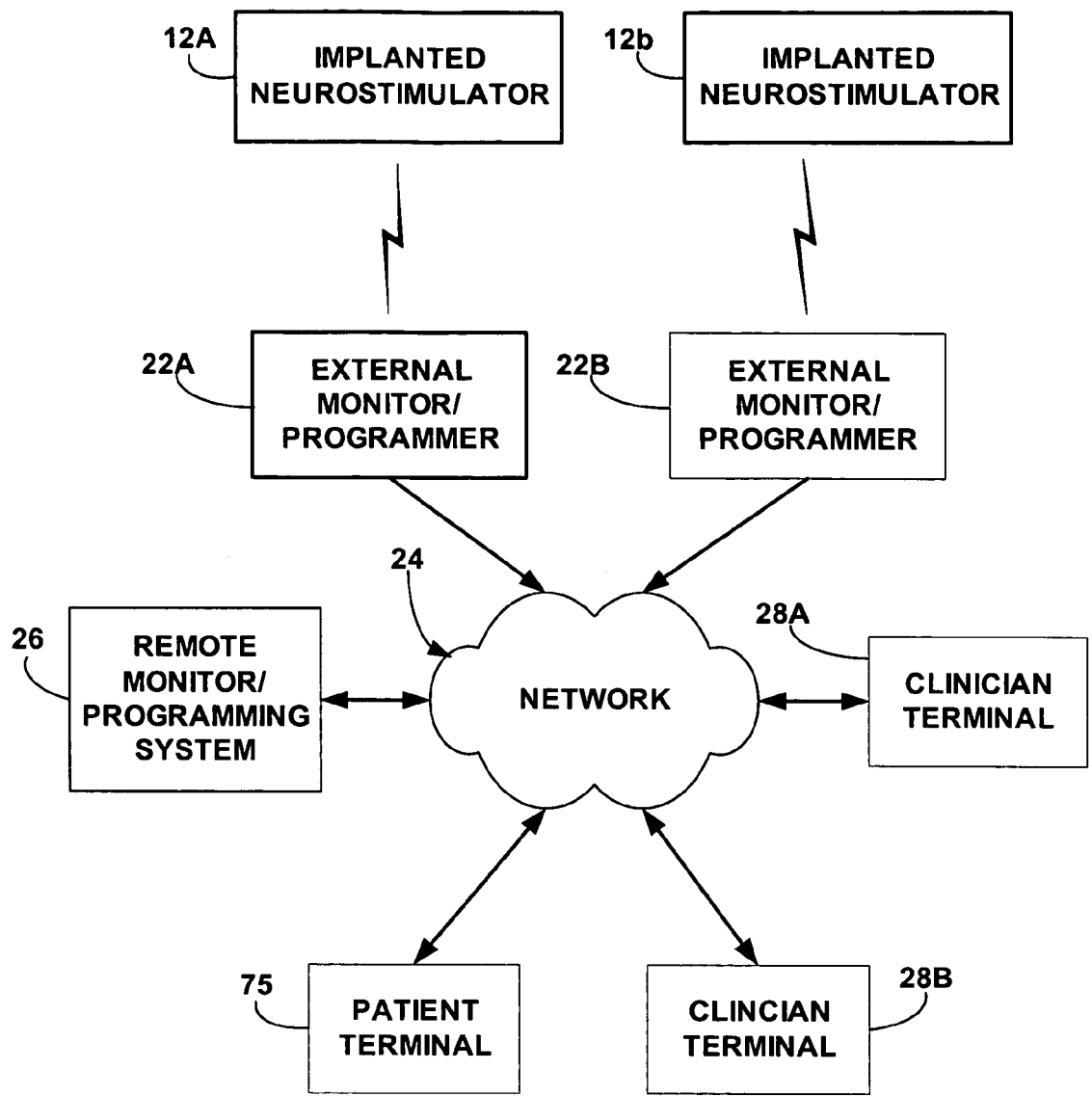
FIG. 6 is block diagram illustrating a system for remote monitoring and programming of implantable neurostimulators.

FIG. 6 is a block diagram illustrating a system for remote monitoring and programming of neurostimulators 12. FIG. 6 generally illustrates the interaction of multiple neurostimulators 12A, 12B with respective external monitor/programmers 22A, 22B, remote monitor/programming system 26, multiple clinician terminals 28A, 28B and, optionally, a patient terminal 75 via network 24. Clinician terminals 28A, 28B permit multiple clinicians to view information for multiple patients 14. The information may include information obtained from sensors 20, neurostimulators 12, and the patients 14 themselves, as well as proposed stimulation parameter adjustments. In some embodiments, multiple clinicians may consult with one another via clinician terminals 28A, 28B. Patient terminal 75 may permit a patient to view a limited set of information, e.g., by viewing patient web pages prepared by remote monitoring/programming system 26.

In some embodiments, the system of FIG. 6, or a similarly constructed system, may be used to support clinical research. For example, external monitor/programmer 22, remote monitoring/programming system 26 and clinician terminals 28A, 28B may permit clinical researchers to access information obtained from implanted neurostimulators 12 for purposes of research, and not necessarily for adjustment of stimulation parameters. Rather, researchers may access the information obtained from external monitor/programmer 22 and remote monitoring/programming system 26 via clinician terminals 28A, 28B to gather information in support of short or long range research for formulation of improved or enhanced therapies.

Figure 7:
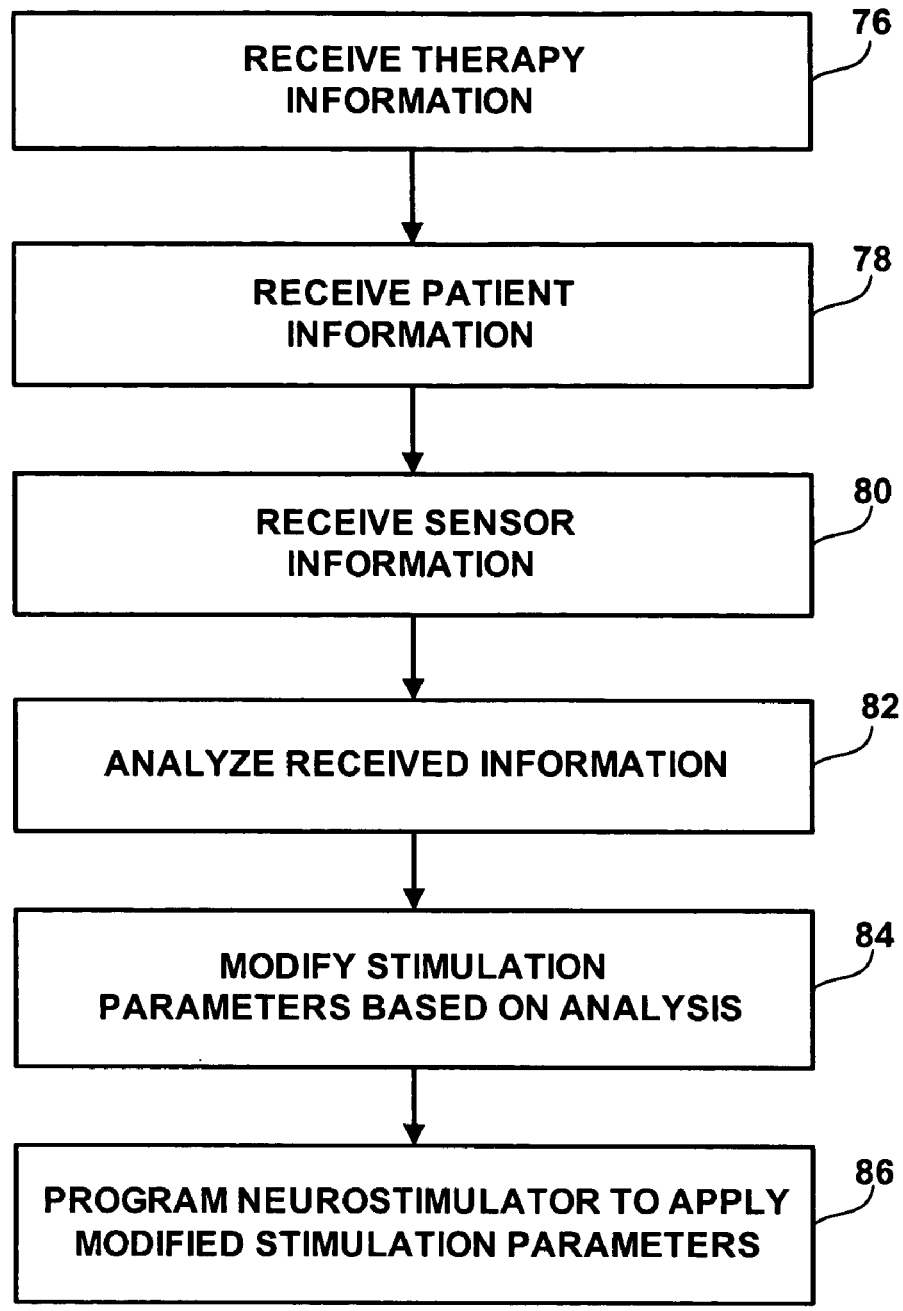
FIG. 7 is flow diagram illustrating operation of an external monitor/programmer to modify neurostimulation parameters based on information obtained from a neurostimulator, an implantable sensor, and a patient.

FIG. 7 is flow diagram illustrating operation of external monitor/programmer 22 to adjust stimulation parameters based on information obtained from a neurostimulator 12, an implantable sensor 20, and a patient 14. As shown in FIG. 7, a processor associated with external monitor/programmer 22 for example may receive therapy information (76) from implanted neurostimulator 12, indicating stimulation parameters associated with neurostimulation therapy delivered by the neurostimulator, as well as the timing of the delivery. Alternatively, such information may already be available within external monitor/programmer 22 by virtue of the fact that external monitor/programmer 22 is responsible for programming neurostimulator 12. However, therapy information may additionally include operational information associated with neurostimulator 12.

In addition, the processor within the external monitor/programmer 22 in this example receives patient information from the patient (78). The patient information may include any of the information exemplified and described above. External monitor/programmer 22 also may receive sensor information (80) in embodiments in which system 10 includes one or more implantable sensors 20. Again, the sensor information may represent physiological conditions within the urinary tract, as exemplified above. Together, the therapy information, patient information, and sensor information may provide an effective representation of the level of efficacy provided by the existing stimulation parameters.

Upon analysis of the received information (82), using a set of adaptation logic, external monitor/programmer 22 may adjust the stimulation parameters (84) presently applied by neurostimulator 12. Alternatively, external monitor/programmer 22 may determine that there is no need to adjust the stimulation parameters. If the stimulation parameters are adjusted, external monitor/programmer 22 programs the neurostimulator 12 by wireless telemetry to apply the modified stimulation parameters. Programming may be entirely automatic or subject to clinician approval. In either case, the adjusted stimulation parameters are selected to enhance the efficacy of the neurostimulation therapy delivered by neurostimulator 12 in alleviating incontinence.

Figure 8:
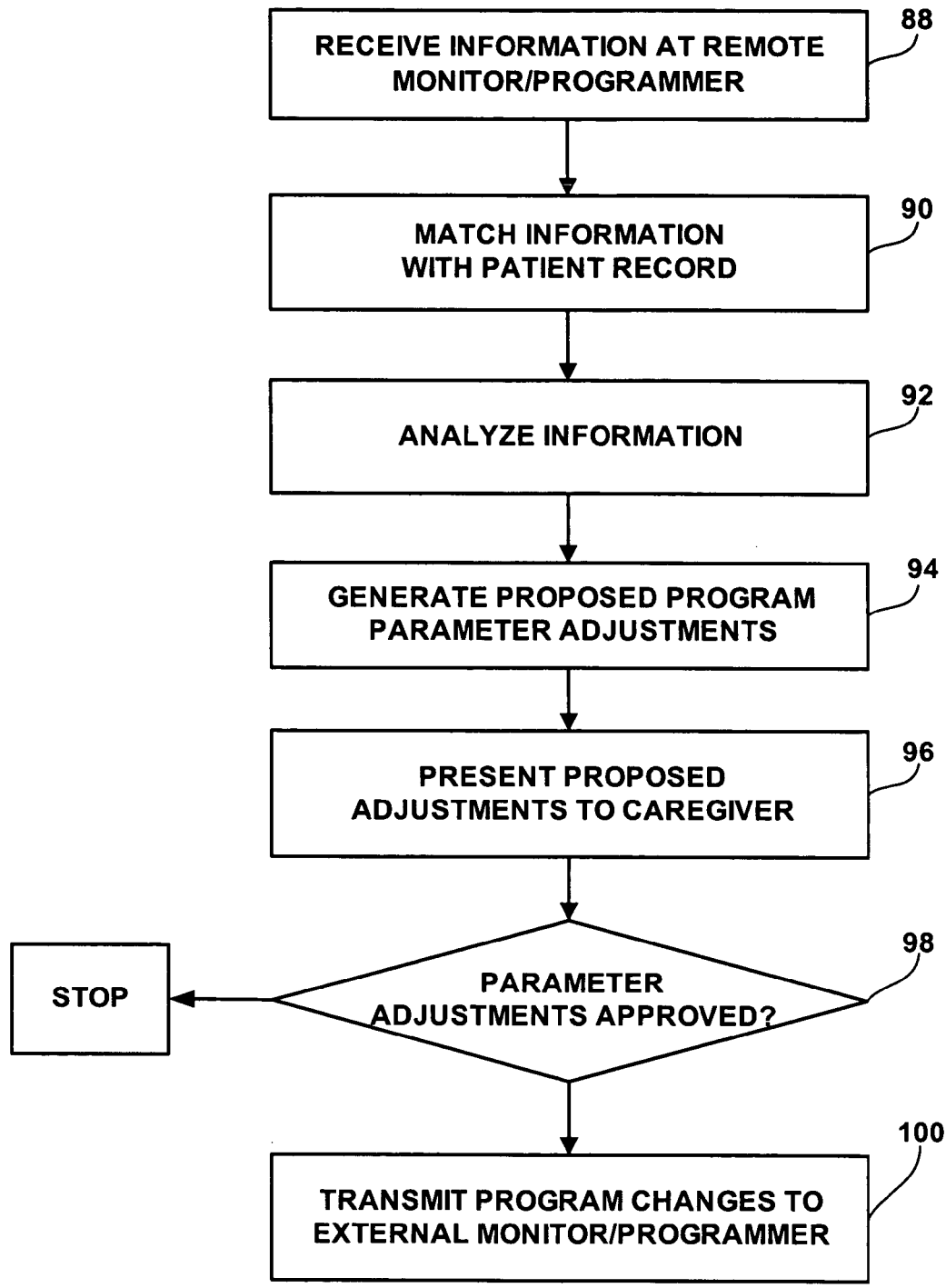
FIG. 8 is flow diagram illustrating operation of a remote programmer to modify neurostimulation parameters based on information obtained from a neurostimulator, an implantable sensor, and a patient.

FIG. 8 is a flow diagram illustrating operation of a remote monitoring/programming system 26 to adjust neurostimulation parameters based on information obtained from a neurostimulator 12, an implantable sensor 20, and a patient 14. As shown in FIG. 8, the processor within the remote monitoring/programming system 26, in this example, receives information from external monitor/programmer 22 (88) and matches the information with a patient record in database 74 (90). Remote monitoring/programming system 26 analyzes the information (92), applying a set of adaptation logic, and generates proposed stimulation parameter adjustments based on the analysis (94).

Remote monitoring/programming system 26 presents the proposed adjustments to a clinician for approval (96). If the adjustments are approved (98), remote monitoring/programming system 26 transmits the adjustments to external monitor/programmer 22 (100), which downloads or inputs the stimulation parameter adjustments into neurostimulator 12. If approval is not obtained, the stimulation parameter adjustments are not loaded into neurostimulator 12, and the process stops. In some embodiments, however, the adjustments may be loaded automatically without approval.

The adaptation logic 43 applied by external monitor/programmer 22 or programming server 76 may be subject to wide variation. In general, the adaptation logic 43 may perform a weighted summation of a selected set of values derived from the information obtained from neurostimulator 12, sensor 20, patient 14, or some combination thereof. In some embodiments, the sum may represent a cost of the present stimulation parameters, in terms of a level of efficacy. If the information indicates that neurostimulator 12 is operating within a desirable range of efficacy, for example, there may be zero cost. If the efficacy level deviates from the desired range, however, the cost increases. The cost may be correlated to adjustments of one or more stimulation parameters to drive the cost back to zero.

As a very simple example, if the information obtained by external monitor/programmer 22 indicates that the patient has experienced N leakage events, the cost function will yield a non-zero cost, as any leakage is generally unacceptable. In this case, the cost function may drive an increase in stimulation frequency to more vigorously stimulate the bladder to avoid involuntary leakage. The increase may be implemented in an instantaneous step change, or in a series of incremental steps.

On the other hand, if there are no leakage events, but physiological information obtained from sensor 20 indicates that sphincter closing pressure is unsatisfactory, or that the bladder is exhibiting an undesirable contractile force, the cost function may yield a non-zero cost, albeit a cost that is much less than the cost resulting from undesirable leakage events. In this case, a less aggressive adjustment in stimulation frequency may be applied as a preemptive measure against possible leakage events.

As another example, activity information entered by patient 14 may indicate that leakage events are more prevalent when the patient is exerting himself at work or during exercise. In this case, based on the number of leakage events and the contractile force of sphincter pressure recorded at the time of such leakage events, stimulation parameters are adjusted to provide more vigorous stimulation during exercise. To that end, the patient may be permitted to select different stimulation programs containing parameters targeted to specific activities of postures.

Although the structure and organization of the adaptation logic 43 may be subject to wide variation, in general, the invention permits delivery of an adaptive neurostimulation therapy that dynamically adjusts to different conditions, and maintains or enhances neurostimulation efficacy for patient 14. An adaptive neurostimulation therapy can be expected to provide more beneficial results for patient 14 relative to static neurostimulation therapies that rely only on fixed clinical programming of stimulation parameters.

In some embodiments, adaptation logic 43 may be configured to apply particular algorithms such as genetic algorithms, Bayesian classification, neural networks, or decision trees. In those cases, adaptation logic 43 may be formulated to implement algorithms similar to those described in U.S. patent application Ser. No. 10/767,674, to Steven M. Goetz, filed Jan. 29, 2004, and entitled "SELECTION OF NEUROSTIMULATOR PARAMETER CONFIGURATIONS USING BAYESIAN NETWORKS," U.S. patent application Ser. No. 10/767,922, to Steven M. Goetz, filed Jan. 29, 2004 and entitled "SELECTION OF NEUROSTIMULATOR PARAMETER CONFIGURATIONS USING NEURAL NETWORKS," U.S. patent application Ser. No. 10/767,545, to Steven M. Goetz, filed Jan. 29, 2004 and entitled "SELECTION OF NEUROSTIMULATOR PARAMETER CONFIGURATIONS USING DECISION TREES," and U.S. patent application Ser. No. 10/767,692, to Steven M. Goetz, filed Jan. 29, 2004 and entitled "SELECTION OF NEUROSTIMULATOR PARAMETER CONFIGURATIONS USING GENETIC ALGORITHMS," the entire content of each of which is incorporated herein by reference.

One embodiment of the invention includes a neurostimulation therapy for incontinence having the steps of receiving, in an external programmer, information relating to the efficacy of neurostimulation therapy delivered by an implanted neurostimulator to manage urinary incontinence; adjusting, in a processor, one or more stimulation settings of the neurostimulation therapy based on the received information and adaptive logic; and inputting the adjusted parameters from the processor to the implanted neurostimulator. A system for performing the above method that includes an external programmer, a processor, and an implantable neurostimulator is also included. Computer-readable medium that includes instructions for carrying out the above method is also included.

Another embodiment of the invention includes a neurostimulation therapy for incontinence having the steps of receiving, in an external programmer, information relating to the efficacy of neurostimulation therapy delivered by an implanted neurostimulator to manage urinary incontinence; sensing, via at least one sensor, information related to the efficacy of neurostimulation therapy delivered by an implanted neurostimulator; adjusting, in a processor, one or more stimulation settings of the neurostimulation therapy based on the received information and adaptive logic; and inputting the adjusted parameters from the processor to the implanted neurostimulator. A system for performing the above method that includes an external programmer, a processor, and an implantable neurostimulator is also included. Computer-readable medium that includes instructions for carrying out the above method is also included.

Another embodiment of the invention includes a neurostimulation therapy for incontinence having the steps of receiving, in a processor, information relating to an implanted neurostimulator to manage urinary incontinence; sensing, via at least one sensor, information related to the efficacy of neurostimulation therapy delivered by an implanted neurostimulator; adjusting, in a processor, one or more stimulation settings of the neurostimulation therapy based on the sensed information, received information and adaptive logic; and inputting the adjusted parameters from the processor to the implanted neurostimulator. A system for performing the above method that includes an external programmer, a processor, and an implantable neurostimulator is also included. Computer-readable medium that includes instructions for carrying out the above method is also included.

Many embodiments of the invention have been described. Various embodiments may be adapted to provide adaptive neurostimulation for other pelvic floor disorder such as fecal incontinence, sexual dysfunction, cystitis, or the like. Accordingly, while the invention has been described in the context of urinary incontinence for purposes of illustration, it is not so limited.

Many embodiments of the invention have been described. These and other embodiments are within the scope of the following claims.

The invention claimed is:
1. A method comprising:
receiving in a processor an operation information from an implantable neurostimulator for delivery of a neurostimulation therapy to manage urinary incontinence, the delivery of the neurostimulation therapy being based on a plurality of stimulation parameters;

sensing, via at least one sensor, sensed information related to the efficacy of the neurostimulation therapy delivered by an implantable neurostimulator;

wirelessly transmitting the sensed information from the sensor to the processor;

selecting, using adaptation logic, at lease one parameter from the plurality of stimulation parameters based on the sensed information and the operation information from the implantable neurostimulator;

determining, in the processor, an adjustment of the at least one parameter;

proposing a modified at least one parameter to a user based, at least in part, on the adjustment of the at least one parameter;

the user choosing a disposition for the modified at least one parameter;

inputting the modified at least one parameter from the processor to the implanted neurostimulator based on the disposition.

2. The method of claim 1, wherein the operation information from the implantable neurostimulator is information regarding the stimulation parameters of the neurostimulator, the elapsed time since the neurostimulator was implanted, the elapsed time since the settings were adjusted, the battery status, the charging status, the lead impedance, the telemetry status, or some combination thereof.

3. The method of claim 2, wherein the information regarding the settings of the implantable neurostimulator is frequency, amplitude, cycling parameters, identification of electrodes that are being utilized, or some combination thereof.

4. The method of claim 1, wherein the sensed information is information regarding the functioning of the bladder, or any other segment of the patient's urinary tract.

5. The method of claim 4, wherein the sensed information relates to bladder pressure, bladder contractile force, urinary sphincter pressure, urine flow rate, urine flow pressure, voiding amount, or some combination thereof.

6. The method of claim 4, wherein the sensed information relates to urine flow velocity, urine or bladder temperature, impedance, urinary pH, or chemical constituency of the urine, or some combination thereof.

7. The method of claim 4, wherein the sensed information relates to a physiological state of the patient.

8. The method of claim 7, wherein the sensed information is cardiac activity, respiratory activity, electromyographic activity, or some combination thereof.

9. The method of claim 7, wherein the sensed information detects a posture or activity level of the patient.

10. The method of claim 1, wherein the processor is associated with the at least one sensor.

11. The method of claim 1, wherein the processor is associated with the implanted neurostimulator.

12. The method of claim 1, wherein the sensed information, the operation information from the implantable neurostimulator, or some combination thereof is sent via wireless telemetry.

13. The method of claim 1, wherein the processor is in communication with a remote programmer.

14. The method as in claim 1, wherein the processor is an external processor.

15. A system for delivering therapy to a patient, comprising:

an implantable neurological stimulator, comprising:
a therapy delivery circuit delivering therapy based on a plurality of stimulation parameters;
a memory module storing said plurality of stimulation parameters and an operating information; and
an implantable neurological stimulator wireless telemetry interface operatively coupled to said memory module;

an implantable sensor, comprising:
a sensing element obtaining sensed information related to efficacy of said therapy; and
a sensor wireless telemetry interface operatively coupled to said sensing element; and a processor receiving said sensed information by way of said sensor wireless telemetry interface and said operating information by way of said implantable neurological stimulator wireless telemetry interface; and a user interface operatively coupled with said processor;

wherein said processor is configured to select, using adaptation logic, at least one parameter from said plurality of parameters based on said sensed information and said operating information;

wherein the processor is further configured to determine an adjustment of said at least one parameter;

wherein said user interface displays a modified at least one parameter to a user based, at least in part, on said adjustment of said at least one parameter;

wherein said user interface is configured to allow said user to select a disposition for said modified at least one parameter; and wherein said modified at least one parameter is stored in said memory module based on said disposition.

16. The system as in claim 15:
further comprising an external programmer having an external wireless telemetry interface in wireless communication with said sensor wireless telemetry interface and said implantable stimulator wireless telemetry interface; and
wherein said processor is a component of said external programmer.

17. The system as in claim 15:
wherein said processor is a component of said implantable neurological stimulator, said processor operatively coupled with said implantable neurological stimulator wireless telemetry interface; and
said implantable neurological stimulator wireless telemetry interface operatively coupled with said sensor wireless telemetry interface.

18. The system as in claim 16, wherein said external programmer comprises an external programmer network link operatively coupled to said external wireless telemetry interface and connecting said external programmer to the internet.

19. The system as in claim 18, further comprising a remote monitor, comprising:
a remote network link, operatively coupled via the internet to said external programmer network link;
a server, said server receiving and storing said sensed information by way of said remote network link, adjusting said at least one stimulation parameter based on said sensed information, and storing said at least one stimulation parameter in said memory module.

20. The system as in claim 19:
further comprising a plurality of said remote stations;
wherein each individual one of said plurality of said remote stations is operatively coupled to other individual ones of said plurality of remote stations via said remote network link.

21. The system as in claim 20 wherein individual ones of said plurality of remote stations is operatively coupled to said external programmer via said remote network link.

22. The system as in claim 15, wherein the processor is an external processor.

* * * * *